(12) United States Patent
Volgas et al.

(10) Patent No.: US 6,831,038 B2
(45) Date of Patent: Dec. 14, 2004

(54) AGRICULTURAL FORMULATION

(75) Inventors: Greg Volgas, Bartlett, TN (US); Johnnie R. Roberts, Memphis, TN (US); Amanda Hayes, Memphis, TN (US)

(73) Assignee: Helena Holding Company, Wilmington, DE (US)

( * ) Notice: Subject to any disclaimer, the term of this patent is extended or adjusted under 35 U.S.C. 154(b) by 0 days.

(21) Appl. No.: 10/081,627

(22) Filed: Feb. 20, 2002

(65) Prior Publication Data

US 2002/0160916 A1 Oct. 31, 2002

Related U.S. Application Data

(60) Provisional application No. 60/270,311, filed on Feb. 20, 2001.

(51) Int. Cl.⁷ .............................. A01N 25/30
(52) U.S. Cl. .................. 504/206; 504/323; 504/324; 504/365; 514/975
(58) Field of Search .............. 504/206, 323, 504/324, 365; 514/975

(56) References Cited

U.S. PATENT DOCUMENTS

| | | | |
|---|---|---|---|
| 4,332,609 A | 6/1982 | Ott ................................ 71/27 |
| 4,478,650 A | 10/1984 | Zado .......................... 148/23 |
| 5,178,795 A | 1/1993 | Roberts ....................... 252/356 |
| 5,234,919 A | 8/1993 | Roberts ....................... 514/119 |
| 5,389,598 A | 2/1995 | Berk et al. .................. 504/206 |
| 5,393,791 A | 2/1995 | Roberts ....................... 514/762 |
| 5,580,567 A | 12/1996 | Roberts ....................... 424/405 |
| 5,725,630 A | 3/1998 | Roberts et al. ................ 71/11 |
| 5,741,502 A | 4/1998 | Roberts ....................... 424/405 |
| 5,877,112 A | 3/1999 | Roberts et al. ............. 504/116 |
| 5,906,961 A | 5/1999 | Roberts et al. ............. 504/116 |
| 6,121,200 A * | 9/2000 | Berger et al. ............... 504/206 |
| 6,329,322 B1 * | 12/2001 | Reierson ..................... 504/206 |
| 6,432,878 B1 * | 8/2002 | Brigance .................... 504/206 |

FOREIGN PATENT DOCUMENTS

| | | |
|---|---|---|
| GB | 1081294 | 8/1967 |
| WO | 00/41567 | 7/2000 |

OTHER PUBLICATIONS

Turner, D.J. "Effects on glyphosate performance of formulation, additives and mixing with other herbicides". Chapter 15 in Th Herbicide Glyphosate. Grossbard et al, eds. p. 221–240. 1985.*

* cited by examiner

Primary Examiner—S. Mark Clardy
(74) Attorney, Agent, or Firm—Connolly Bove Lodge & Hultz LLP

(57) ABSTRACT

The invention pertains to new composition and a method for increasing the solubility of various agricultural compounds in water at a low pH. The compounds included in this patent are typically not soluble at pH ranges less than 7 to produce commercially viable liquid concentrates. This method requires the use of amine-containing surfactants and organic acids to lower the pH of various compounds and also keep them soluble in water.

60 Claims, No Drawings

AGRICULTURAL FORMULATION

RELATED APPLICATIONS

This application claims benefit to U.S. Provisional Ser. No. 60/270,311 filed Feb. 21, 2001 which is incorporated by reference in its entirety for all useful purposes.

BACKGROUND OF THE INVENTION

Many agricultural formulations contain water-soluble salts. These salts, often alkylamine salts, are generally not as active as their acid equivalents. For example, 2,4-Dichlorophenoxyacetic acid (2,4-D acid) is known to be more herbicidally active than the dimethylamine salt of 2, 4-D. However, 2, 4-D acid is not soluble in water. Solvents used to formulate 2,4-D acid are known to be phytotoxic to plants and enhance herbicide volatility and subsequent drift to non-target areas. In another example, boron is known to be available to plants only in the boric acid form. However, boric acid is only soluble at relatively low concentrations in water, while the Monoethanolamine salt of boric acid is known to be much more soluble.

U.S. Pat. No. 4,332,609 issued to Ott, which is incorporated by reference in its entirety, discusses the means of producing just such a water-soluble concentrate of boric acid and Monoethanolamine. The disadvantage is that the plants must convert this boric acid Monoethanolamine complex to boric acid in order to use it. Furthermore, boron is often applied in conjunction with a variety of agricultural pesticides that are subject to degradation at high pH ranges. The boric acid Monoethanolamine salt produces high pH solutions and therefore is detrimental to many pesticides.

U.S. Pat. No. 5,877,112 assigned to Helena Chemical Company, which is incorporated by reference in its' entirety, decribes a composition containing (a) at least one acid ester surfactant (phosphate ester surfactants)
(b) at least one amine containing surfactant
(c) and at least one water soluble agricultural chemical.

The formulation is expensive, largely because of the addition of phosphate ester surfactants. It would be beneficial if there were alternative, less expensive ways of obtaining formulation stability than using phosphate esters. Furthermore, the phosphate ester surfactants contribute to the eye irritation severity of the overall formulation.

U.S. Pat. No. 5,389,598 assigned to Monsanto Company, which is incorporated by reference in its entirety, describes a storage stable aqueous composition containing
(a) water-soluble pesticide or plant growth modifying agent,
(b) an alkylamine surfactant,
(c) a $C_6$–$C_{22}$ saturated or unsaturated alkyl monocarboxylic or dicarboxylic acid
(d) and water.

The third ingredient (c) $C_6$–$C_{22}$ saturated or unsaturated alkyl monocarboxylic or dicarboxylic acid is essential and must be present in a ratio alkoxylated alkylamine surfactant to $C_6$–$C_{22}$ saturated alkyl mono or dicarboxylic acid from at least about 2:1. The ratio of glyphosate to carboxylic acid is from about 10:1 (a) to about 100:1 and preferably about 10:1 to 40:1. Fattyamine ethoxylates have been known to be used in agricultural formulations in the past. Specifically, tallowamine ethoxylate surfactant is known to enhance glyphosate activity and translocation.

WO 00/41567 describes the use of an adjuvant composition containing
(a) polyoxyalkylene aliphatic amine
(b) an eye irritation reducing compound (carboxylic acid)
(c) mixture of polyhydric alcohols preferably a trihydric alcohol and at least one diol such as ethylene glycol or propylene glycol.

The carboxylic acid is present in an amount from about 0.05 to about 5 wt. % of the adjuvant. When the adjuvant is used with glyphosate, the amount of carboxylic acid in the formulation is from about 0.2 to about 0.4% wt. %.

We have found that the invention can work without a polyhydric alcohol or a mixture of polyhydric alcohols. Furthermore, the invention can be practiced with an eye irritating amount of carboxylic acid which is the opposite taught by WO 00/41567.

SUMMARY OF THE INVENTION

The present invention is a composition comprising (a) a carboxylic acid or phosphorous containing acid providing that the phosphorous containing acid is not a glyphosate,
(b) an amine containing surfactant,
(c) at least one water soluble agricultural chemical with the proviso that the composition contains less than 3 percent by weight of phosphate ester surfactant. It is more preferable, that there is less than about 1 percent by weight of phosphate ester surfactant and most preferable there is no phosphate ester surfactant present. We have found that the invention can work without a polyhydric alcohol or a mixture of polyhydric alcohols. Furthermore, the invention can be practiced with an eye irritation amount of carboxylic acid. The amount of the carboxylic acid used is preferably an eye irritating amount greater which would be greater than 0.4 wt. %. More preferably, the amount of the carboxylic acid is at least 1%, and even more preferably at least 4 wt. % and even more preferably at least 6 wt. % and most preferably at least 7 wt. %.

The present invention is also a homogenous agricultural liquid composition containing at least (a) a carboxylic acid or phosphorus containing acid, (b) an amine containing surfactant, preferably a fatty amine ethoxylate surfactant, (c) and at least one other agricultural chemical without substantially no or no acid ester surfactants such as phosphate ester surfactants.

The agricultural chemical referred to herein, can used in agricultural or non-agricultural applications. The agricultural applications include, but are not limited to pesticide, fertilizer, or plant growth regulators. The non-agricultural applications include, but are not limited to forestry, aquatics, right of way (such as the areas along roads or medians), turf (such as lawns, golf courses etc.) ornamental (such as plants for their beauty) or municipal (parks, school, open land, etc).

The present invention works with substantially no or no phosphate ester surfactant. The preferred embodiment can have a weight/weight ratio of glyphosate to carboxylic acid less than about 10:1 and more preferably less 8:1 and most preferably less than about 7:1. The glyphosate and carboxylic acid are most preferably in a weight/weight ratio of glyphosate to carboxylic acid in a 8:1 to about 2:1.

A further embodiment of the invention is a composition comprising:
(a) a phosphorous containing acid providing that the phosphorous containing acid is not a glyphosate, (b) an amine containing surfactant of the formula:

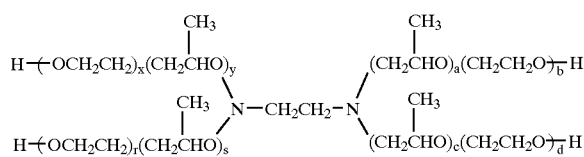

where x,y,a,b,c,d,r, and s are independently a number from 0–100, with e proviso that the sum of a+b+c+d+r+s+x+y must be at least 4, (c) at least one water soluble agricultural chemical with the proviso that the composition contains less than 3 percent by weight o phosphate ester surfactant.

Optionally, other surfactants or formulation aids can be added. The formulation can have a pH of less than about 7. It is also possible to add a buffering agent to further decrease the pH of the composition.

Preferably, if a carboxylic acid is used, the acid is a monocarboxylic acid, a dicarboxylic acid and a tricarboxylic acid. The acid is formic acid, acetic acid, propionic acid, butyric acid, valeric acid, oxalic acid, malonic acid, succinic acid, glutaric acid, citric acid and phosphoric acid, preferably, citric acid. If a phosphorus containing acid is used, preferably it is phosphoric acid or phosphorous acid. Preferably the amine containing surfactant is a fatty amine and most preferably a tallowamine ethoxylate. The composition allows water-soluble salts of agricultural chemicals to remain stable and soluble at lower than normal pH ranges.

DETAILED DESCRIPTION OF THE PREFERRED EMBODIMENT

It has been surprisingly discovered that a wide range of water soluble compounds can be stabilized at lower than normal pH ranges using a combination of phosphorus containing acids or monocarboxylic, dicarboxylic or tricarboxylic acids and amine containing surfactants such as, but not limited to fatty amine ethoxylates.

The phosphorus containing acids are for the purposes of this patent, considered non-surfactants. That is, the surface tension for these acids is greater than 60 dynes/m as measured by a Du Nuoy Surface Tensiometer at a concentration of 1–10%.

Preferably, the phosphorus containing acid is phosphoric acid or phosphorous acid. The commercial grades of these acids contain anywhere from 50–85% pure $H_3PO_4$ or $H_3PO_3$.

The monocarboxylic acids are of the formula

wherein x is 1 to 5.

The dicarboxylic acids are of the formula

wherein x is 2 to 5.

Any tricarboxylic acid is effective.

The amine containing surfactants can be, but are not limited to fatty amine alkoxylates or block copolymers derived from the sequential addition of ethylene oxide and optionally propylene oxide to form ethylenediamines.

The fatty amine alkoxylates are of the formula:

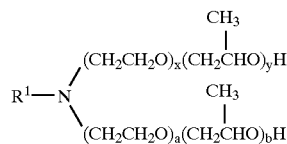

wherein $R^1$ is a $C_8$–$C_{22}$ alkyl group, x, y, a, and b are identical or different and are a number from 0 to 100 with the proviso that x+y+z+b is at least 2. The most preferred fatty amine alkoxylate surfactant is a tallowamine ethoxylate. The fatty amine containing surfactant can be present in an amount from about 1 to about 99%. Preferably, the fatty amine containing surfactant is present in an amount sufficient to enhance the efficacy of the crop protection chemicals.

The block copolymer derived from the sequential addition of ethylene oxide and propylene oxide to ethylenediamine is of the formula:

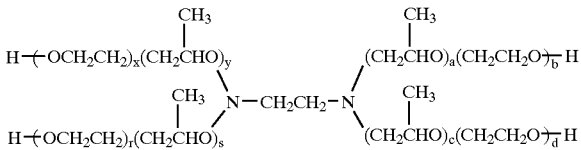

where x, y, a, b, c, d, r, and s are identical or different are a number from 0 to 100, with the proviso that the sum a+b+c+d+r+s+x+y must be at least 2. The most preferred fatty amine alkoxylate surfactant is a tallowamine ethoxylate. The fatty amine containing su surfactant can be present in an amount from about 1 to about 99%. Preferably, the fatty amine containing surfactant is present in an amount sufficient to enhance the efficacy of the crop protection chemicals.

The agricultural chemical can be a fertilizer containing boron, zinc, copper, iron, blends of nitrogen phosphorous and potash or mixtures thereof. The fertilizer can be ammonia sulfate, an ammonia salt of a carboxylic acid, mono- or di-potassium phosphate, a micronutrient, ammonia nitrate, urea, ammonia citrate or ammonia acetate.

The agricultural chemical can be a crop protecting chemical such as, but not limited to a herbicide, insecticide or fungicide. The herbicide can be, but not limited to, dimethylamine (DMA) salt of 2,4-dichlorophenoxyacetic acid, DMA salt of dicamba, sodium salt of dicamba, isopropylamine (IPA) salt of glyphosate, IPA salt of 2,4-dichlorophenoxyacetic acid, sodium salt of acifluorfen, sodium-salt of bentazon, sodium salt of imazethapyr, ammonium salt of imazaquin, IPA salt of imazapyr, sodium salt of asulam or mixtures thereof. The agricultural chemical can be present in an amount from about 1 to about 99%.

The composition can contain micronutrients such as, but not limited to a water soluble salt of boron, iron, manganese, magnesium, copper or zinc. In example I, Ott's patented composition of a monoethanolamine salt of boric acid is further unexpectedly improved by using a blend of phosphate ester and an amine surfactant such as tallowamine ethoxylate.

The agricultural formulation can also contain additional surfactants. The preferred additional surfactants include, but are not limited to:

a) sorbitan fatty acid ester, b) polyethoxylated derivative of a sorbitan fatty acid ester, c) fatty alkanolamides
e) silicone surfactants
f) ethoxylated fatty
g) alkyl ethoxylates
h) alkylphenol
i) polypropylene glycols
j) tristyrylphenol alkoxylates,
k) amine ethoxylates
l) N-Acyl Sarcosines and Sodium N-Acyl Sarcosinates,
m) alkylaryl polyethoxy carboxylate ester,
n) tristyrylphenol alkoxylate carboxylate esters,
o) alkylpolyglucosides.

Additionally, buffering agents can be added to the composition to further reduce the pH. The buffering agents include, but are not limited to,
a) glutaric acid,
b) gluconic acid,
c) lactic acid,
d) glycolic acid,
e) acrylic acid,
f) carboxylated alcohol ethoxylate,
g) ethoxylated alkylphenol carboxylate esters;
h) tristyrylphenol alkoxylate phosphate esters;
i) tristyrylphenol alkoxylate carboxylate esters; and
j) fatty acids and blends thereof and The formulation can optionally contain water insoluble agricultural chemicals, such as but not limited to, pesticides. The pesticides can be, but are not limited to ester of dichlorophenoxyacetic acid, trifluralin, pendimethalin, propanil, atrazine, benefin, chloroimuron, linuron, alachlor, metalochlor or mixtures thereof.

Furthermore the agricultural formulation can have a surface tension of less than 60 dynes as measured by the Du Nuoy Surface Tensiometer at a concentration of 1–10%.

The formulation is made by mixing all the ingredients together. Other optional ingredients include but are not limited to dyes, thickeners, anti-corrosion agent, anti-caking agents, stabilizers, gel inhibitors, anti-freezes, anti-foam agents, mixtures thereof and the like.

The following examples are listed to help illustrate the advantage of the new agricultural formulation. All the examples are described in a percent by weight basis.

EXAMPLE 1

| Ingredients | % in formula |
| --- | --- |
| Monoethanolamine salt of boric acid | 80.0 |
| Tallowamine ethoxylate surfactant | 10.0 |
| Citric acid | 10.0 |

The improvement of this formula is in the resulting pH of the composition. The monoethanolamine salt of boric acid has a pH of 9.0 on its own. The composition of Example 1 has a pH of about 7.0. It is generally acknowledged in most agricultural applications that plants can only use boron in it's acidic form.

The patented composition can contain pesticides such as the dimethylamine salt of 2,4-Dichlorophenoxyacetic acid (2,4-D Amine). In Example 2, the water-soluble agricultural chemical is the dimethylamine salt of 2,4-D, the tricarboxylic acid is citric acid, the amine containing surfactant is tallowamine ethoxylate, and the other surfactants are wetting agents. The resulting composition has a pH of about 6.0, as opposed to conventional dimethylamine salt of 2,4-D formulations which have a pH of about 8.5. The formulation in Example 2 produced a nice clear solution.

EXAMPLE 2

| Ingredients | % in formula |
| --- | --- |
| Dimethylamine salt of 2,4-D | 69.90 |
| Tallowamine ethoxylate surfactant | 13.40 |
| Citric acid | 10.40 |
| Alcohol ethoxylate surfactant | 2.80 |
| Water | 3.50 |

In Example 3, the water-soluble agricultural chemical is the dimethylamine salt of 2,4-D, the carboxylic acid is acetic acid, the amine containing surfactant is tallowamine ethoxylate, and the other surfactants are alcohol ethoxylates.

EXAMPLE 3

| Ingredients | % in formula |
| --- | --- |
| Dimethylamine salt of 2,4-D | 69.90 |
| Tallowamine ethoxylate surfactant | 13.40 |
| Acetic acid (glacial) | 10.40 |
| Alcohol ethoxylate surfactant | 2.80 |
| Water | 3.50 |

In Example 4, the water-soluble agricultural chemical is the dimethylamine salt of dicamba, the tricarboxylic acid is citric acid, the amine containing surfactant is tallowamine ethoxylate, and the other surfactants are wetting agents.

EXAMPLE 4

| Ingredients | % in formula |
| --- | --- |
| Dimethylamine salt of dicamba | 69.90 |
| Tallowamine ethoxylate surfactant | 13.40 |
| Citric acid | 10.40 |
| Alcohol ethoxylate surfactant | 2.80 |
| Water | 3.50 |

In Example 5, the water-soluble agricultural chemical is the dimethylamine salt of 2,4-D, the carboxylic acid is propionic acid, the amine containing surfactant is tallowamine ethoxylate, and the other surfactants are wetting agents.

EXAMPLE 5

| Ingredients | % in formula |
| --- | --- |
| Dimethylamine salt of 2,4-D | 69.90 |
| Tallowamine ethoxylate surfactant | 13.40 |
| Propionic acid | 10.40 |
| Alcohol ethoxylate surfactant | 2.80 |
| Water | 3.50 |

In Example 6, the water-soluble agricultural chemical is the isopropylamine salt of glyphosate, the tricarboxylic acid is citric acid, the amine containing surfactant is tallowamine ethoxylate, and the other surfactants are wetting agents.

EXAMPLE 6

| Ingredients | % in formula |
| --- | --- |
| Isopropylamine salt of glyphosate | 69.90 |
| Tallowamine ethoxylate surfactant | 13.40 |
| Citric acid | 10.40 |
| Alcohol ethoxylate surfactant | 2.80 |
| Water | 3.50 |

In Example 7, the water-soluble agricultural chemical is the isopropylamine salt of glyphosate, the carboxylic acid is acetic acid, the amine containing surfactant is tallowamine ethoxylate.

EXAMPLE 7

| Ingredients | % in formula |
| --- | --- |
| Isopropylamine salt of glyphosate | 69.90 |
| Tallowamine ethoxylate surfactant | 13.40 |
| Acetic acid | 10.40 |
| Water | 6.30 |

In Example 8, the water-soluble agricultural chemical is the dimethylamine salt of 2,4-D, the carboxylic acid is ascorbic acid, the amine containing surfactant is a block copolymer of EO and PO forming an ethylenediamine, and the other surfactants are wetting agents.

EXAMPLE 8

| Ingredients | % in formula |
| --- | --- |
| Dimethylamine salt of 2,4-D | 69.90 |
| Tallowamine ethoxylate surfactant | 13.40 |
| Ascorbic acid | 10.40 |
| Alcohol ethoxylate surfactant | 2.80 |
| Water | 3.50 |

The inventive composition can be used in a method of controlling vegetation by adding the inventive composition to foliage of plants. Further, the inventive composition can be used in a method of promoting plant growth and/or eliminating the damage caused by insects by adding the inventive composition to foliage of plants. This invention would normally be introduced into some carrier such as water, fertilizer or oil.

The following patents and reference, which include several ingredients that can be used according to this invention, are incorporated by reference in its entirety for all useful purposes:

U.S. Pat. No. 5,741,502 Homogeneous, essentially nonaqueous adjuvant compositions with buffering capability
U.S. Pat. No. 5,725,630 Dry granular fertilizer blend and a method of fertilizing plants
U.S. Pat. No. 5,580,567 Homogeneous, essentially nonaqueous adjuvant compositions with buffering capability
U.S. Pat. No. 5,393,791 Homogeneous, essentially nonaqueous adjuvant compositions with buffering capability
U.S. Pat. No. 5,234,919 Water soluble, highly active dimethoate formulations in an alcohol/ester solvent system
U.S. Pat. No. 5,178,795 Homogeneous, essentially nonaqueous adjuvant compositions with buffering capability
U.S. Pat. No. 5,906,961 Alkanolamide spreader-sticker surfactant combination
U.S. Pat. No. 5,877,112 Agricultural formulation All the references discussed in this application are incorporated by reference in their entirety for all useful purposes.

While there is shown and described certain specific structures embodying the invention, it will be manifest to those skilled in the art that various modifications and rearrangements of the parts may be made without departing form the spirit and scope of the underlying inventive concept and that the same is not limited to the particular forms herein shown and described.

We claim:

1. A composition comprising:
   (a) a carboxylic acid in an eye irritating amount, phosphorous acid or phosphoric acid
   (b) an amine containing surfactant and
   (c) at least one water soluble agricultural chemical,
   with the proviso that the composition contains no phosphate ester surfactant and the proviso that if a carboxylic acid and glyphosate are present, then said glyphosate and carboxylic acid are in a weight/weight ratio a glyphosate to carboxylic acid in a 8:1 to about 2:1.

2. The composition as claimed in claim 1, wherein said carboxylic acid is a mono-carboxylic acid of the formula $C_xH_{2x}O_2$, where x=1 to 5.

3. The composition as claimed in claim 2, wherein said mono-carboxylic acid is formic acid, acetic acid, propionic acid, butyric acid or valeric acid.

4. The composition as claimed in claim 1, wherein said carboxylic acid is a di-carboxylic acid of the formula $C_xH_{2x-2}O_4$, where x=2 to 5.

5. The composition as claimed in claim 4, wherein said di-carboxylic acid is oxalic acid, malonic acid, succinic acid or glutaric acid.

6. The composition as claimed in claim 1, wherein said carboxylic acid is a tri-carboxylic acid.

7. The composition as claimed in claim 6, wherein said tri-carboxylic acid is citric acid.

8. The composition as claimed in claim 1, wherein component (a) is phosphoric avid.

9. The composition as claimed in claim 1, wherein component (a) is phosphorous acid.

10. The composition as claimed in claim 1, wherein said amine-containing surfactant is a fatty amine alkoxylate of the formula:

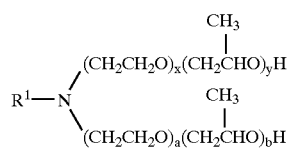

wherein $R^1$ is a $C_a$–$C_{22}$ allyl group,
x,y,a, and b are independently a number from 0 to 100 with the proviso that x+y+a+b is at least 2.

11. The composition as claimed in claim 10, wherein said fatty amine alkoxylate is tallowamine ethoxylate.

12. The composition as claimed in claim 1, wherein said water-soluble agricultural chemical is a fertilizer.

13. The composition as claimed in claim 12, wherein said fertilizer is ammonia sulfate, ammonia salt of a carboxylic acid mono-potassium phosphate or di-potassium phosphate, ammonia nitrate, urea, ammonia citrate or ammonia acetate.

14. The composition as claimed in claim 12, wherein said fertilizer is a micronutrient.

15. The composition as claimed in claim 14, wherein said micronutrient is a water soluble salt of zinc, copper, manganese, magnesium, iron or boron.

16. The composition as claimed in claim 1, wherein the composition contains no mixtures of polyhydric alcohol.

17. The composition as claimed in claim 1, wherein said water soluble agricultural chemical is a pesticide.

18. The composition as claimed in claim 17, wherein said pesticide is a herbicide, insecticide and fungicide.

19. The composition as claimed in claim 18, wherein said herbicide is chlorinated carboxylic acid herbicide.

20. The composition as claimed in claim 18, wherein said herbicide is glyphosate or a salt thereof.

21. The composition as claimed in claim 18, wherein said herbicide is glyphosate-tritium or a salt thereof.

22. The composition as claimed in claim 18, wherein said herbicide is glufosinate or a salt thereof.

23. The composition as claimed in claim 18, wherein said herbicide is synthetic auxin.

24. The composition as claimed in claim 23, wherein said synthetics is chloramben or dicamba or salts thereof.

25. The composition as claimed in claim 23, wherein said synthetic auxin is a an unsubstitued phenoxy carboxylic acid, 2,4-dichlorophenoxy acetic acid, 2,4,5-trichlorophenoxy acetic acid, 2,4-dichlorophenoxy butyric acid, clomeprop, dichlorprop, dichlorprop-P, monochlorophenoxy acetic acid, monochlorophenoxy butyric acid, mecoprop, or mecoprop-P or salts thereof.

26. The composition as claimed in claim 23, wherein said synthetic auxin is 2,4-dichlorophenoxy acetic acid, 2,4,5-trihlorophenoxy acetic acid, 2,4-dichlorophenoxy butyric acid, clomeprop, dichlorprop, dichlorprop-P, monochlorophenoxy acetic acid, monochlorophenoxy butyric acid, mecoprop or mecoprop-P or salts thereof.

27. The composition as claimed in claim 23, wherein said synthetic auxin is a pyridine carboxylic acid.

28. The composition, as claimed in claim 23, wherein said synthetic auxin is a quinoline carboxylic acid.

29. The composition as claimed in claim 23, wherein said synthetic auxin is clopyralid, fluroxypyr, piclorain or triclopyr or salts thereof.

30. The composition as claimed in claim 23, wherein said synthetic auxin is a quiclorac or quinmerac or salts thereof.

31. The composition as claimed in claim 23, wherein said synthetic auxin is a phenoxy carboxylic acid.

32. The composition as claimed in claim 1, wherein said amine containing surfactant is a block copolymer derived from the sequential addition of ethylene oxide and optionally propylene oxide to ethylenediamine, of the formula:

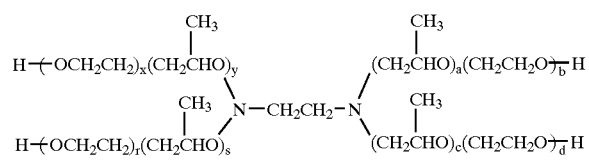

where x,y,a,b,c,d,r, and s are independently a number from 0–100, with the proviso that the seam of a+b+c+d+r+s+x+y must be at least 4.

33. A composition comprising:
(a) phosphorous acid or phosphoric acid
(b) an amine containing surfactant and
(c) at least one water soluble agricultural chemical, with the proviso that the composition contains no phosphate ester surfactant.

34. The composition as claimed in claim 33, wherein said component (a) is phosphoric acid.

35. The composition as claimed in claim 33, wherein said component (a) is phosphorous acid.

36. The composition as claimed in claim 33, wherein said amine-containing surfactant is a fatty amine alkoxylate of the formula:

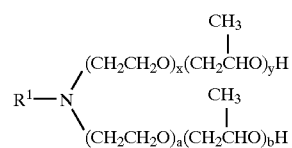

wherein $R^1$ is a $C_8$–$C_{22}$ alkyl group, x,y,a, and b independently a number from 0 to 100 with the proviso that x+y+a+b is at least 2.

37. The composition as claimed in claim 33, wherein said amine surfactant is tallowamine ethoxylate.

38. The composition as claimed in claim 33, wherein said water-soluble agricultural chemical is a fertilizer.

39. The composition as claimed in claim 38, wherein said fertilizer is ammonia sulfate, ammonia salt of a carboxylic acid, mono-potassium phosphate, di-potassium phosphate, ammonia nitrate, urea, ammonia citrate or ammonia acetyl.

40. The composition as claimed in claim 38, wherein said fertilizer is a micronutrient.

41. The composition as claimed in claim 40, wherein said micronutrient is a water soluble salt of zinc, copper, manganese, magnesium, iron or boron.

42. The composition as claimed in claim 33, wherein said water soluble agricultural chemical is a pesticide.

43. The composition as claimed in claim 42, wherein said pesticide is a herbicide, insecticide or fungicide.

44. The composition as claimed in claim 43, wherein said pesticide is a chlorinated carboxylic acid herbicide.

45. The composition as claimed in claim 43, wherein said pesticide is glyphosate or a salt thereof.

46. The composition as claimed in claim 43, wherein said herbicide is glyphosate-trimesiun or a salt thereof.

47. The composition as claimed in claim 43, wherein said herbicide is glufosinate or a salt thereof.

48. The composition as claimed in claim 43, wherein said herbicide is a synthetic auxin.

49. The composition as claimed in claim 48, wherein said synthetic auxin is chloramben or dicamba or salts thereof.

50. The composition as claimed in claim 48, wherein said synthetic auxin is chloramben or dicamba or salts thereof.

51. The composition as claimed in claim 48, wherein said synthetic auxin is a phenoxy carboxylic acid, 2,4-dichlorophenoxy acetic acid, 2,4,5-trichlorophenoxy acetic acid, 2,4-dichlorophenoxy butyric acid, clomeprop, dichlorprop, dichlorprop-P, monochlorophenoxy acetic acid, monochlorophenoxy butyric acid, mecoprop, or mecoprop-P or salts thereof.

52. The composition as claimed in claim 48, wherein said synthetic auxin is 2,4-dichlorophenoxy acetic acid, 2,4,5-trichlorophenoxy acetic acid, 2,4-dichlorophenoxy butyric acid, clomeprop, dichlorprop, dichlorprop-P, monochlorophenoxy acet acid, monochlorophenoxy butyric acid, mecoprop or mecoprop-P or salts thereof.

53. The composition as claimed in claim 48, wherein said synthetic auxin is a pyridine carboxylic arid, clopyralid, fluroxypyr, pioloram or triclopyr or salts thereof.

54. The composition as claimed in claim 48, wherein said synthetic auxin is a quinoline carboxylic acid, quiclorac or quinmerac or salts thereof.

55. The composition as claimed in claim 33, wherein said anime containing surfactant is a block copolymer derived from the sequential addition of ethylene oxide and optionally propylene oxide to ethylenediamine, of the formula:

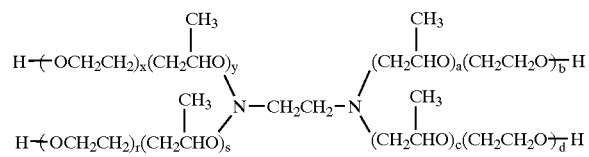

where x,y,a,b,c,d,r, and s are independently a number from 0–100, with the proviso that the sum of a+b+c+d+r+s+x+y must be at least 4.

56. A composition comprising:

(a) phosphorous acid or phosphoric acid, (b) an amine containing surfactant of the formula:

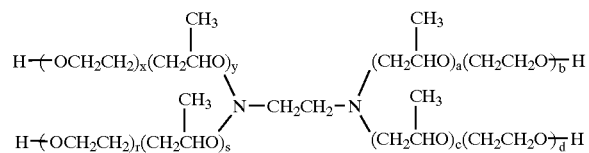

where x,y,a,b,c,d,r, and s are independently a number from 0–100, with the proviso that the sum of a+b+c+d+r+s+x+y must be at least 4 and (c) at least one water soluble agricultural chemical, with the proviso that the composition contains no phosphate ester surfactant.

57. A composition comprising of:

(a) a carboxylic acid, phosphorous acid or phosphoric acid, (b) an amine containing surfactant and (c) at least one water soluble agricultural chemical, with the proviso that the composition contains no phosphate ester surfactant and the proviso that if a carboxylic acid is used for said component (a) then said carboxylic acid is present in an amount that does not effectively reduce eye irritation.

58. A method for treating soil which comprises adding the composition as claimed in claim 57 to the soil.

59. A method for treating soil which comprises adding the composition as claimed in claim 1 to the soil.

60. A method for treating soil which comprises adding the composition as claimed in claim 33 to the soil.

* * * * *

UNITED STATES PATENT AND TRADEMARK OFFICE
CERTIFICATE OF CORRECTION

PATENT NO. : 6,831,038 B2
DATED : December 14, 2004
INVENTOR(S) : Greg Volgas et al.

It is certified that error appears in the above-identified patent and that said Letters Patent is hereby corrected as shown below:

Title page,
Item [74], *Attorney, Agent or Firm* "Hultz" should read -- Hutz --.

Column 8,
Line 43, "avid" should read -- acid --.
Line 57, "$C_8$-$C_{22}$ allyl" should read -- $C_8$-$C_{22}$ alkyl --.

Column 9,
Line 16, "tritium" should read -- trimesium --.
Line 22, "synthetics" should read -- synthetic auxin --.
Line 24, "a" should be deleted.
Line 63, "phasphorous" should read -- phosphorous --.

Column 10,
Line 16, "and b" should read -- and b are --.
Line 25, "acetyl" should read -- acetate --.

Signed and Sealed this

Seventeenth Day of May, 2005

JON W. DUDAS
*Director of the United States Patent and Trademark Office*